(12) United States Patent
Fan et al.

(10) Patent No.: US 11,414,658 B2
(45) Date of Patent: Aug. 16, 2022

(54) TRACER PARTICLE AND METHOD OF USING THE SAME AND METHOD OF MANUFACTURING THE SAME

(71) Applicant: Industrial Technology Research Institute, Hsinchu (TW)

(72) Inventors: Kai-Chun Fan, Tainan (TW);
Yin-Lung Han, Tainan (TW);
Pei-Jyuan Gao, Kaohsiung (TW);
Yong-Yang Lin, Tainan (TW);
Chieh-Lun Cheng, Taoyuan (TW);
Chien-Chang Huang, Taichung (TW);
Yung-Ho Chang, Taichung (TW);
Chia-Long Lin, Taipei (TW); I-Son Ng, Tainan (TW); Bo-Han Chen, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 343 days.

(21) Appl. No.: 16/710,632

(22) Filed: Dec. 11, 2019

(65) Prior Publication Data

US 2020/0199585 A1     Jun. 25, 2020

(30) Foreign Application Priority Data

Dec. 25, 2018   (TW) .................................. 107146933
Nov. 27, 2019   (TW) .................................. 108143130

(51) Int. Cl.
*C12Q 1/68*     (2018.01)
*C12N 15/11*    (2006.01)
*C12Q 1/6876*   (2018.01)

(52) U.S. Cl.
CPC ............ *C12N 15/11* (2013.01); *C12Q 1/6876* (2013.01)

(58) Field of Classification Search
CPC ........................................................ C12Q 1/68
USPC .............................................................. 435/6
See application file for complete search history.

(56) References Cited

U.S. PATENT DOCUMENTS

| 9,194,226 B2 | 11/2015 | Blair |
| 9,206,683 B2 | 12/2015 | Blair et al. |
| 9,322,056 B2 | 4/2016 | Mccann et al. |
| 9,675,953 B2 | 6/2017 | Oldenburg et al. |

(Continued)

FOREIGN PATENT DOCUMENTS

| CN | 101952546 A | 1/2011 |
| CN | 103751110 A | 4/2014 |

(Continued)

OTHER PUBLICATIONS

Nandiyanto et al., "Synthesis of spherical mesoporous silica nanoparticles with nanometer-size controllable pores and outer diameter", Microporous and Mesoporous Materials, vol. 120, 2009, pp. 447-453.

(Continued)

*Primary Examiner* — Aaron A Priest
(74) *Attorney, Agent, or Firm* — Birch, Stewart, Kolasch & Birch, LLP

(57) ABSTRACT

A tracer particle is provided. The tracer particle includes: a core structure; a nucleic acid molecule immobilized on the core structure; and a shell layer covering the core structure and the nucleic acid molecule; wherein the core structure has a first porosity, the shell layer has a second porosity, and the first porosity is greater than the second porosity.

21 Claims, 11 Drawing Sheets

Specification includes a Sequence Listing.

(56) References Cited

U.S. PATENT DOCUMENTS

| | | | |
|---|---|---|---|
| 2004/0018559 A1* | 1/2004 | Lau | B01J 20/3293 |
| | | | 435/7.1 |
| 2013/0064776 A1* | 3/2013 | El Harrak | G01N 33/582 |
| | | | 435/7.1 |
| 2013/0210018 A1 | 8/2013 | Garnett | |
| 2016/0243262 A1* | 8/2016 | Ortac | C12Q 1/00 |
| 2018/0105422 A1* | 4/2018 | Yu | B01J 20/28021 |
| 2018/0119220 A1 | 5/2018 | Grass et al. | |

FOREIGN PATENT DOCUMENTS

| | | |
|---|---|---|
| EP | 2 024 763 B1 | 9/2015 |
| TW | 200502549 A | 1/2005 |
| TW | I307331 B | 3/2009 |
| TW | I333067 B | 11/2010 |
| WO | WO 2012/020230 A1 | 2/2012 |

OTHER PUBLICATIONS

Paunescu et al., "Detecting and Number Counting of Single Engineered Nanoparticles by Digital Particle Polymerase Chain Reaction", ACS Nano, vol. 9, No. 10, 2015, pp. 9564-9572.

Paunescu et al., "Protection and Deprotection of DNA—High-Temperature Stability of Nucleic Acid Barcodes for Polymer Labeling", Angew. Chem. Int. Ed., vol. 52, 2013, pp. 4269-4272.

Puddu et al., "Magnetically Recoverable, Thermostable, Hydrophobic DNA/Silica Encapsulates and Their Application as Invisible Oil Tags", ACS Nano, vol. 8, No. 3, 2014, pp. 2677-2685.

Zhang et al., "DNA Barcoding for Fractured Reservoir Analysis—An Initial Investigation", Proceedings of 42st Workshop on Geothermal Reservoir Engineering, Stanford University, Sanford, California, Feb. 13-15, 2017, 9 pages total.

Zhang et al., "Uniquely Identifiable DNA-Embedded Silica Nanotracer for Fractured Reservoir Characterization", Proceedings of 41st Workshop on Geothermal Reservoir Engineering, Stanford University, Sanford, California, Feb. 22-24, 2016, 10 pages total.

Mikutis. G., et al, "Silica-Encapsulated DNA-Based Tracers for Aquifer Characterization," Environ. Sci. Technol., 2018, vol. 52, pp. 12142-12152.

Moller, K., et al., "Highly efficient siRNA delivery from core-shell mesoporous silica nanoparticles with multifunctional polymer caps†," Nanoscale, 2016. vol. 8, pp. 4007-4019.

Paunescu, D., et al, "Reversible DNA encapsulation in silica to produce ROS-resistant and heatresistant synthetic DNA 'fossils'," Nature Protocols, 2013, vol. 8, No. 12, pp. 2440-2448.

* cited by examiner

TRACER PARTICLE AND METHOD OF USING THE SAME AND METHOD OF MANUFACTURING THE SAME

CROSS REFERENCE TO RELATED APPLICATIONS

This application claims priority of Taiwanese Patent Application No. 107146933, filed on Dec. 25, 2018 and Taiwanese Patent Application No. 108143130, filed on Nov. 27, 2019, the entirety of which are incorporated by reference herein.

REFERENCE TO SEQUENCE LISTING SUBMITTED VIA EFS-WEB

This application includes an electronically submitted sequence listing in .txt format. The .txt file contains a sequence listing entitled "0941-4159PUS1 ST25.txt" created on Feb. 5, 2020 and is 1,159 bytes in size. The sequence listing contained in this .txt file is part of the specification and is hereby incorporated by reference herein in its entirety.

TECHNICAL FIELD

The present disclosure relates to a tracer particle, and in particular it relates to a tracer particle containing a nucleic acid molecule, a method for using the same, and a method of manufacturing a tracer particle.

BACKGROUND

Tracer technology can be used as a tool for monitoring fluids, pollution leaks and product tracking. It is currently widely used in exploration for geothermal sources, natural gas and petroleum, which can improve the extraction efficiency of the above energy sources. Tracer technology can also be used as tools for groundwater source tracking and tracers in environmental protection remediation.

The types of tracers that are currently in common use include radioactive tracers, fluorescent tracers, chemical tracers and so on. However, their types are limited, analysis procedures are complicated, and their toxicity may cause harm to the environment. In view of these problems, the development of new tracers has drawn much attention. The biological tracer is a new generation of tracer, which uses biological materials as the main indicators (tags, fingerprints), and is not toxic, and less likely to cause environmental pollution. However, the resistance of existing biotracers to extreme environments is not quite satisfactory, and it is difficult to apply them to extreme environmental conditions such as environments of strong acid, strong alkali or high temperature.

As described above, although the tracers currently available have been substantially adequate for their intended purposes, they have not been satisfactory in all aspects.

SUMMARY

In accordance with some embodiments of the present disclosure, a tracer particle is provided. The tracer particle includes: a core structure; a nucleic acid molecule immobilized on the core structure; and a shell layer covering the core structure and the nucleic acid molecule; wherein the core structure has a first porosity, the shell layer has a second porosity, and the first porosity is greater than the second porosity.

In accordance with some embodiments of the present disclosure, a method for using a tracer particle is provided. The method for using the tracer particle includes: providing the aforementioned tracer particle; placing the tracer particle in a fluid to be observed; collecting a sample of the fluid, recovering the tracer particle from the sample and releasing the nucleic acid molecule from the tracer particle; and analyzing the nucleic acid molecule that has been released.

In accordance with some embodiments of the present disclosure, a method of manufacturing a tracer particle is provided. The method of manufacturing the tracer particle includes: forming a core structure; immobilizing a nucleic acid molecule on the core structure; and forming a shell layer on the core structure to cover the core structure and the nucleic acid molecule. In addition, the step of forming the core structure includes: providing an oil phase solution including a precursor of silicon and a co-emulsifier; providing an aqueous phase solution including water and a surfactant; and adding the oil phase solution to the aqueous solution to form a mixed solution; adding a catalyst to the mixed solution; and heating the mixed solution.

In order to make the features or advantages of the present disclosure more obvious and easy to understand, a detailed description is given in the following embodiments with reference to the accompanying drawings.

DETAILED DESCRIPTION

Figure 1:
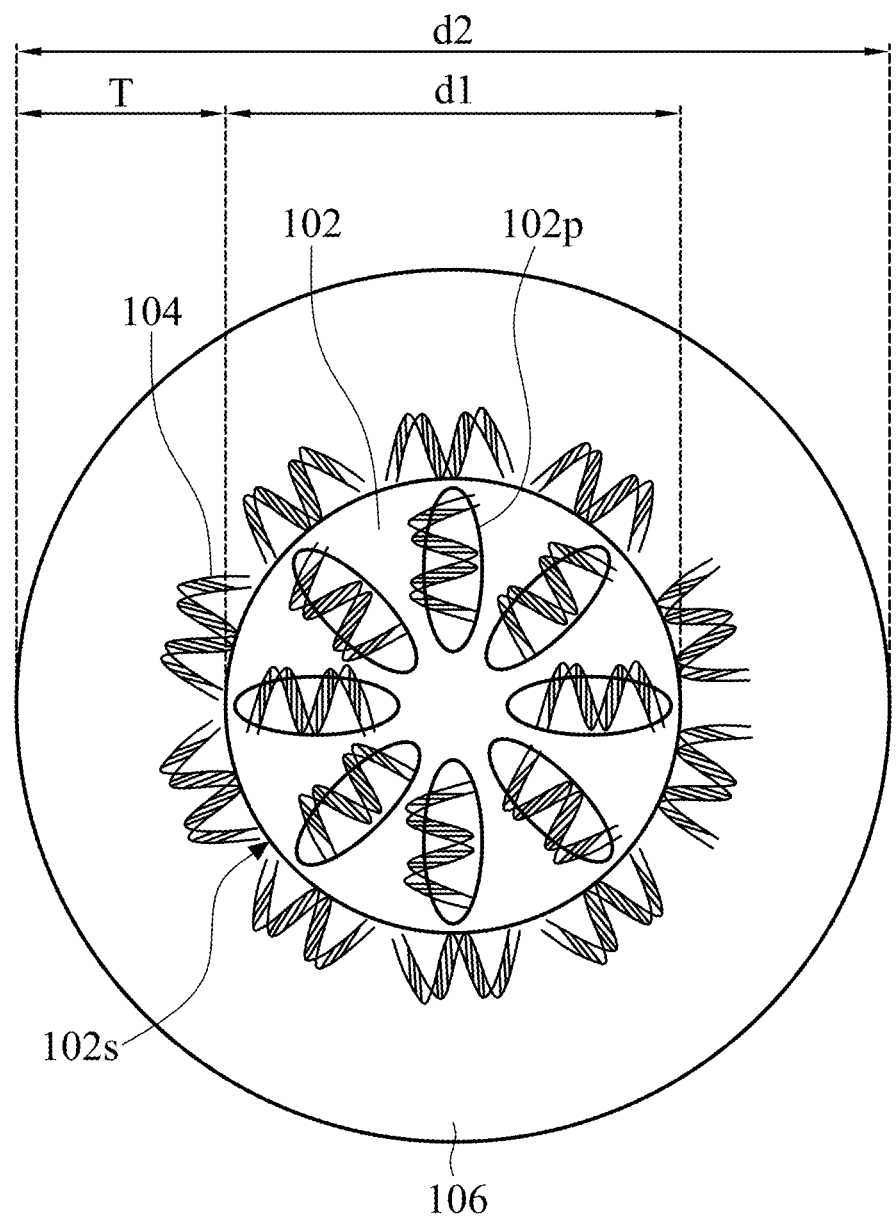
FIG. 1 is a structural diagram of the tracer particle in accordance with some embodiments of the present disclosure.

The tracer particle of the embodiments of the present disclosure, the method for using the same and the method of manufacturing the tracer particle are described in detail in the following description. It should be understood that in the following detailed description, for purposes of explanation, numerous specific details and embodiments are set forth in order to provide a thorough understanding of the present disclosure. The specific elements and configurations described in the following detailed description are set forth in order to clearly describe the present disclosure. However, it will be apparent that the exemplary embodiments set forth herein are used merely for the purpose of illustration, and the concept of the present disclosure may be embodied in various forms without being limited to those exemplary embodiments. In addition, similar and/or corresponding reference numerals may be used to indicate similar and/or corresponding elements in different embodiments to clearly describe the present disclosure. However, the use of these similar and/or corresponding reference numerals is only for simply and clearly describing some embodiments of the disclosure, and does not suggest any correlation between the different embodiments and/or structures discussed.

It should be understood that, elements or devices of the drawings may exist in various forms well known to those skilled in the art. In addition, it should be understood that although the terms "first", "second", "third" etc. may be used herein to describe various elements, components, regions, layers, or portions, these elements, components, regions, layers, or portions should not be limited by these terms. These terms are only used to distinguish one element, component, region, layer, or portion from another element, component, region, layer, or portion. Thus, a first element, component, region, layer, or portion discussed below could be termed a second element, component, region, layer or portion without departing from the teachings of the present disclosure.

The terms "about", "approximately" and "substantially" typically mean +/−20% of the stated value, more typically mean +/−10% of the stated value, more typically +/−5% of the stated value, or +/−3% of the stated value, or +/−2% of the stated value, or +/−1% of the stated value, or +/−0.5% of the stated value. The stated value of the present disclosure is an approximate value. When there is no specific description, the stated value includes the meaning of "about", "approximately" or "substantially".

The description of the exemplary embodiments is intended to be read in connection with the accompanying drawings, which are to be considered part of the entire written description. It should be understood that the drawings are not drawn to scale. In fact, elements may be arbitrarily enlarged or reduced so that the features of the present disclosure can be clearly expressed.

Unless defined otherwise, all terms (including technical and scientific terms) used herein have the same meaning as commonly understood by one of ordinary skill in the art to which the present disclosure belongs. It should be appreciated that, in each case, the term, which is defined in a commonly used dictionary, should be interpreted as having a meaning that conforms to the relative skills of the present disclosure and the background or the context of the present disclosure, and should not be interpreted in an idealized or overly formal manner unless so defined.

In accordance with some embodiments of the present disclosure, a tracer particle is provided, which includes a specific nucleic acid molecule as an indicator. In addition, the tracer particle includes a core structure having a relatively large porosity to increase the immobilization strength of the nucleic acid molecule and improve the thermal conductivity of the particle, thereby improving the resistance of the tracer particle to extreme environments.

FIG. 1 is a structural diagram of a tracer particle 10 in accordance with some embodiments of the present disclosure. It should be understood that additional features may be added to the tracer particle 10 in accordance with some embodiments. Referring to FIG. 1, the tracer particle 10 may include a core structure 102, a nucleic acid molecule 104 and a shell layer 106. The core structure 102 may serve as a carrier of the tracer particle 10 to carry other structures subsequently formed. The nucleic acid molecules 104 may be immobilized on the core structure 102. The nucleic acid molecules 104 may include specific nucleic acid sequences and may be used as an indicator for the tracer particle 10. Furthermore, the shell layer 106 may cover the core structure 102 and the nucleic acid molecules 104, which may serve as a protective and encapsulating structure.

As shown in FIG. 1, in some embodiments, the core structure 102 may include a plurality of holes 102p, and the nucleic acid molecules 104 may be immobilized in the holes 102p. Specifically, in some embodiments, a portion of the nucleic acid molecules 104 may be immobilized in the holes 102p of the core structure 102, and a portion of the nucleic acid molecules 104 may be immobilized on the surface 102s of the core structure 102.

In particular, the core structure 102 having holes 102p may improve the thermal conductivity of the tracer particle 10, making it suitable for high temperature environments. In addition, the immobilization strength of the nucleic acid molecules 104 on the core structure 102 may also be increased. In some embodiments, the core structure 102 has a first porosity, and the first porosity may be in a range from about 2 nm to about 100 nm, or from about 4 nm to about 40 nm. It should be understood that the porosity of the core structure 102 should not be too large, or the effect of protecting the nucleic acid molecules 104 may not be achieved. On the other hand, the porosity of the core structure 102 should not be too small, or there may be no sufficient space for attachment of the nucleic acid molecules 104, thereby reducing the immobilization efficiency of the nucleic acid molecules 104.

In some embodiments, the particle size d1 of the core structure 102 may be in a range from about 20 nm to about 9000 nm, from about 20 nm to about 200 nm, from about 30 nm to about 100 nm, or from about 200 nm to about 9000 nm. In accordance with some embodiments, the aforementioned particle size may be a volume-based particle size.

The core structure 102 may be formed of an inorganic material. In some embodiments, the material of the core structure 102 may include silicon dioxide, silicates, carbonates such as calcium carbonate, nano-gold, metal oxides, heat-resistant polymers such as polyethylene glycol or polystyrene, high molecular weight polymers such as polylactic acid, or a combination thereof.

In some embodiments, the surface of the core structure 102 may be modified to immobilize the nucleic acid molecules 104 on the core structure 102. Specifically, a quaternary ammonium salt containing chlorine may be used so that the surface of the core structure 102 may be positively charged, and therefore may be connected to the core structure 102 that is negatively charged. In some embodiments, the quaternary ammonium salt containing chloride may include N-methyl-3-aminopropyltrimethoxyalkane (trimethoxy[3-(methylamino)propyl]silane, TMAPS).

In addition, the core structure 102 may include deoxyribonucleic acid (DNA), ribonucleic acid (RNA), peptide nucleic acid (PNA), or a combination thereof. In some embodiments, the nucleic acid molecule 104 may include a double-stranded helical DNA. In some embodiments, the nucleic acid molecule 104 may include a plasmid.

In some embodiments, the length of the nucleic acid molecule 104 may be in a range from about 10 base pairs (bp) to about 2000 base pairs, or from about 50 base pairs to about 500 base pairs. In the embodiment where the nucleic acid molecule 104 is a plasmid, the length of the nucleic acid molecule 104 may be in a range from about 1500 base pairs to about 10,000 base pairs, or from about 2000 base pairs to about 4000 base pairs. It should be understood that when the length of the nucleic acid molecule 104 is too long, the shell layer 106 may not be able to completely cover the nucleic acid molecule 104, or it may require a long time to complete the coating, which increases the difficulty of the encapsulation process. On the other hand, when the length of the nucleic acid molecule 104 is too short, the nucleic acid molecule 104 may decompose easily, reducing the sequence specificity of the nucleic acid molecule 104, thereby making the identification of the indicator poor. Moreover, in accordance with some embodiments, the nucleic acid molecule 104 existing in plasmid form may protect the target nucleic acid fragment (calibration object), and may assist in increasing of the tolerance and recovery of the tracer particle 10 in extreme environments. In addition, the nucleic acid molecule 104 existing in plasmid form may also simplify the purification steps and have the advantage of being easy to operate.

In some embodiments, the nucleic acid molecule 104 having any suitable sequence may be designed as an indicator. For example, in some embodiments, in order to improve the temperature tolerance of the nucleic acid molecule 104, the sequence of the designed nucleic acid molecule 104 may include a part of the nucleic acid sequence of *Thermos thermophilus*. For example, in some embodiments, the thermophile may include *Tepidimonas fonticaldi, Tepidimonas ignava, Tepidimonas aquatica, Bacillus stearothermophilus, Thermoactinomyces vulgaris, Therms aquaticus, Thermococcus, Thermotoga, Sulfolobus, Thermoproteus, Desulfurolobus, Acidianus, Pyrodictium occultum, Pyrodictium brockii, Methanopyrus* or *Pyrobaculum*, but it is not limited thereto.

Furthermore, in some embodiments, the sequence of the designed nucleic acid molecule 104 may include a part of the nucleic acid sequence of algae. For example, in some embodiments, the algae may include *Chlamydomonas reinhardtii, Chlamydomonas moewusii, Chlamydomonas eugametos, Chlamydomonas segnis*, etc., which belong to *Chlamydomonas; Dunaliella salina, Dunaliella tertiolecta, Dunaliella primolecta*, etc., which belong to *Dunaliella; Chlorella vulgaris, Chlorella pyrenoidosa*, etc., which belong to *Chlorella; Haematococcus pluvialis*, etc., which belong to *Haematococcus; Chlorococcum littorale*, etc., which belong to *Chlorococcum; Pseudochoricystis ellipsoidea*, etc., which belong to *Pseudochoricystis; Amphora* sp., etc., which belong to *Amphora; Nitzschia alba, Nitzschia closterium, Nitzschia laevis*, etc., which belong to *Nitzschia; Crypthecodinium cohnii*, etc., which belong to *Crypthecodinium; Euglena gracilis, Euglena proxima*, etc., which belong to *Euglena; Paramecium bursaria*, etc., which belong to *Paramecium; Synechococcus aquatilis, Synechococcus elongatus*, etc., which belong to *Synechococcus; Spirulina platensis, Spirulina subsalsa*, etc., which belong to *Spirulina; Prochlorococcus marinus*, etc., which belong to *Prochlorococcus; Oocystis polymorpha*, etc., which belong to *Oocystis*, but it is not limited thereto.

In some embodiments, the designed nucleic acid molecule 104 may have a hybrid nucleic acid sequence. In some embodiments, the sequence of the designed nucleic acid molecule 104 may include a part of the nucleic acid sequence from prokaryotes and be a part of the nucleic acid sequence from eukaryotes, e.g., parts of the nucleic acid sequences from thermophiles and algae. For example, in some embodiments, the sequence of the nucleic acid molecule 104 may include a part of the sequence of the 16 S rDNA of thermophile and a part of the sequence of the 18 S rDNA of algae. Since there should be no organisms possessing the sequence characteristics of both species in the natural environment, the sequence including the nucleic acid molecule 104 from both prokaryotes and eukaryotes should have specificity. Such the sequence of nucleic acid molecule 104 renders the tracer particles easily identified and the possibility of interference with nucleic acid fragments in the environment can be reduced. Specifically, in some embodiments, the sequence of the designed nucleic acid molecule 104 may include parts of the nucleic acid sequences of *Tepidimonas fonticaldi* and *Chlamydomonas reinhardtii*.

In addition, in some embodiments, the region of the sequence having a higher content of cytosine (C) and guanine (G) than Adenine (A) and Thymine (T) may be selected as the sequence of the nucleic acid molecule 104. Since the force between cytosine and guanine is stronger than that between adenine and thymine, the melting temperature is higher and the thermal stability is better when the GC content of the sequence is higher. Specifically, in some embodiments, the GC content of the sequence of the designed nucleic acid molecule 104 may be in a range from about 55% to about 70%.

In some embodiments, the sequence of the nucleic acid molecule 104 and the sequence of SEQ ID No. 1 may have a sequence similarity of at least 85%, 90%, or 95%. In some embodiments, the nucleic acid molecule 104 may include the sequences as shown in SEQ ID Nos. 2 and 3. Furthermore, in the embodiments where the nucleic acid molecule 104 is a plasmid, the nucleic acid molecule 104 may include a nucleic acid fragment inserted in the plasmid, and the sequence of the nucleic acid fragment and the sequence of SEQ ID No. 1 may have a sequence similarity of at least 85%, 90% or 95%.

In addition, the common technique known in the art may be used to design the nucleic acid sequence and manufacture the nucleic acid molecule 104. For example, primers complementary to the designed nucleic acid sequence may be used to amplify the designed nucleic acid sequence in large quantities by polymerase chain reaction (PCR). In some embodiments, the bio-fermentation technology may be further used to increase the yield of the nucleic acid molecules 104. Specifically, a suitable plasmid may be selected, and a designed nucleic acid fragment (for example, SEQ ID No. 1) may be inserted into the plasmid to construct a recombinant plasmid. The host cells containing the recombinant plasmid then may be cultured in large quantities by using a fermentation tank. In some embodiments, the host cell may include *Escherichia coli*. In some embodiments, the recombinant plasmids containing a target nucleic acid fragment may be extracted from the host cells using an alkaline lysis method. For example, in accordance with some embodiments, the production of nucleic acid molecules 104 in a four-liter fermentation tank may achieve a yield of about 8.85 mg/day, which is far more than the yield of nucleic acid molecules 104 prepared by PCR (about 0.4 mg/day).

As described above, the shell layer 106 may be used as an encapsulating material to cover the core structure 102 and the nucleic acid molecule 104. In some embodiments, the shell layer 106 has a second porosity. In some embodiments, the first porosity of the core structure 102 is greater than the second porosity of the shell layer 106. In some embodiments, the second porosity of the shell layer 106 may be substantially 0 nm. That is, the shell layer 106 may substantially have no holes, and may be a solid or dense shell layer, which may completely encapsulate the nucleic acid molecule 104 and prevent the nucleic acid molecule 104 from being exposed. In some embodiments where the second porosity of the shell layer 106 is zero, the tracer particle 10 may be applied to the detection of a fluid. In some other embodiments, the second porosity of the shell layer 106 is not zero, for example, the second porosity may be in a range from about 0.5 nm to about 10 nm. In some embodiments where the second porosity of the shell layer 106 is not zero, the tracer particle 10 may be applied to the detection of air.

In addition, the shell layer 106 may have a single-layer structure or a multilayer structure. As shown in FIG. 1, in some embodiments where the shell layer 106 has a single-layer structure, the shell layer 106 may substantially have no holes and may be substantially encapsulated.

In some embodiments, the thickness T of the shell layer 106 may be in a range from about 10 nm to about 5000 nm, or from about 10 nm to about 150 nm, or from about 50 nm to about 120 nm.

In some embodiments, the shell layer 106 may include silicon dioxide, silicates, carbonates such as calcium carbonate, heat-resistant polymers such as polyethylene glycol or polystyrene, high molecular weight polymers such as polylactic acid, or a combination thereof. In some embodiments, the core structure 102 and the shell layer 106 may be formed of the same material.

In some embodiments, a quaternary ammonium salt containing chlorine may be used to modify the core structure 102 having the nucleic acid molecule 104 immobilized thereon so that the interior of the shell layer 106 may be positively charged and connected to the negatively charged nucleic acid molecule 104 to form a closed shell-core structure. In some embodiments, the quaternary ammonium salt containing chlorine may include N-methyl-3-aminopropyltrimethoxyalkane(trimethoxy[3-(methylamino)propyl]silane, TMAPS).

Furthermore, as shown in FIG. 1, in some embodiments, the particle diameter d2 of the tracer particle 10 after the encapsulation process is completed may be in a range from about 30 nm to about 10,000 nm, or from about 30 nm to about 300 nm, or from about 50 nm to about 150 nm. In accordance with some embodiments, the aforementioned particle size may be a volume-based particle size.

In addition, in some embodiments, the tracer particle 10 after encapsulation may have good homogeneity, that is, have a uniform shape, size, or particle size. In some embodiments, the size variation of the tracer particle 10 may be in a range from about 0% to about 10%.

Figure 2:
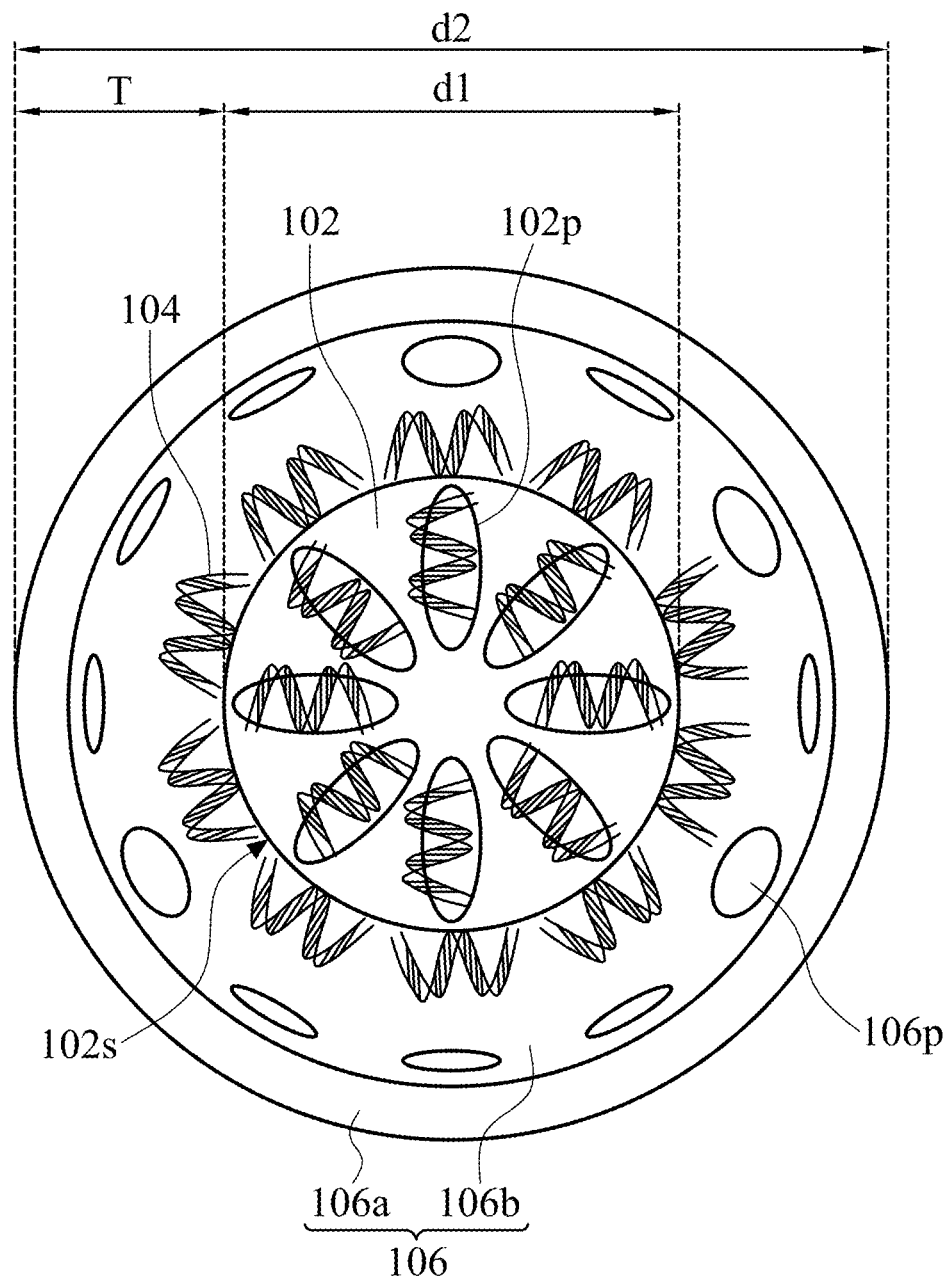
FIG. 2 is a structural diagram of the tracer particle in accordance with some embodiments of the present disclosure.

Next, refer to FIG. 2, which is a structural diagram of a tracer particle 20 in accordance with some other embodiments of the present disclosure. It should be understood that the same or similar components or elements in the following context will be denoted by the same or similar reference numerals, and their materials, manufacturing methods and functions are the same as or similar to those described in the above context, and thus will not be repeated herein. The tracer particle 20 of the embodiment shown in FIG. 2 is substantially similar to the tracer particle 10 shown in FIG. 1. The difference between them is that the shell layer 106 of the tracer particle 20 has a multilayer structure.

Specifically, in this embodiment, the shell layer 106 may include an outer shell layer 106a and an inner shell layer 106b. As shown in FIG. 2, in this embodiment, the inner shell layer 106b may include a plurality of holes 106p. The holes 106p may reduce the thermal conductivity of the shell layer 106, thereby improving the temperature resistance of the tracer particle 20. In some embodiments, the porosity of the inner shell layer 106b may be in a range from about 4 nm to about 40 nm. In addition, in this embodiment, the outer shell layer 106a substantially has no holes, and the nucleic acid molecule 104 can be entirely encapsulated and prevent the nucleic acid molecule 104 from being exposed.

It should be understood that although in the embodiment shown in FIG. 2, the shell layer 106 includes two layers, i.e. the outer shell layer 106a and the inner shell layer 106b, in some other embodiments, the shell layer 106 may have other suitable numbers of sub-layers. Furthermore, although the inner shell layer 106b includes the holes 106p in the embodiment shown in FIG. 2, in some other embodiments, the inner shell layer 106b may substantially have no holes.

In accordance with some embodiments, the tracer particles provided in the present disclosure can be operated in an environment of 120° C. for at least 5 hours. In accordance with some embodiments, the tracer particles provided in the present disclosure can be operated in an environment of 120° C. for more than 24 hours, and can maintain a recovery rate of more than 80%. In accordance with some embodiments, the tracer particles provided in the present disclosure can be operated in an environment of 120° C. for more than 720 hours, and can maintain a recovery rate of more than 20%. In accordance with some embodiments, the tracer particles provided in the present disclosure can be operated in an environment having a pH value of 1 to 13 for at least 720 hours. For example, the operation can be performed in an environment having a pH value of 1, 2, 3, 4, 5, 6, 7, 8, 9, 10, 11, 12, or 13 for at least 720 hours.

In addition, in accordance with some embodiments, the tracer particles provided in the present disclosure may be used for fluid tracking and exploration of geothermal source or oil wells. Specifically, tracer particles can track the movement (flow, migration, travel) of fluids in the fractured areas of the stratification and can be recovered, thereby the distribution and state of oil wells or gas wells can be analyzed. In accordance with some embodiments, the tracer particles provided in the present disclosure can also be used for tracking pollutants. In accordance with some embodiments, the tracer particles provided in the present disclosure can be used as anti-counterfeiting labels.

In addition, in accordance with some embodiments, a method for using a tracer particle is provided. The method may include the following steps: providing the tracer particle described in the previous embodiments; placing the tracer particle in a fluid to be observed; collecting a sample of the fluid, recovering the tracer particle from the sample and releasing the nucleic acid molecule from the tracer particle; and analyzing the nucleic acid molecule that has been released. In some embodiments, the tracer particles can be continuously operated in a fluid of 120° C. for at least 720 hours. In accordance with some embodiments, the tracer particles can be continuously operated in a fluid having a pH value of 1 to 13 for at least 720 hours.

In some embodiments, hydrofluoric acid may be used to remove the shell layer of the tracer particle to release and desorb the nucleic acid molecules from the tracer particle. In some embodiments, the concentration of the aqueous hydrofluoric acid solution (HF/NH$_4$F) may be in a ranging from about 0.5 (v/v) % to about 3.0 (v/v) %, e.g., about 1.5 (v/v) %. In some embodiments, the released nucleic acid molecules may be analyzed by real-time polymerase chain reaction (q-PCR) to confirm the presence or absence of the designed specific nucleic acid molecule and its concentration.

Figure 3:
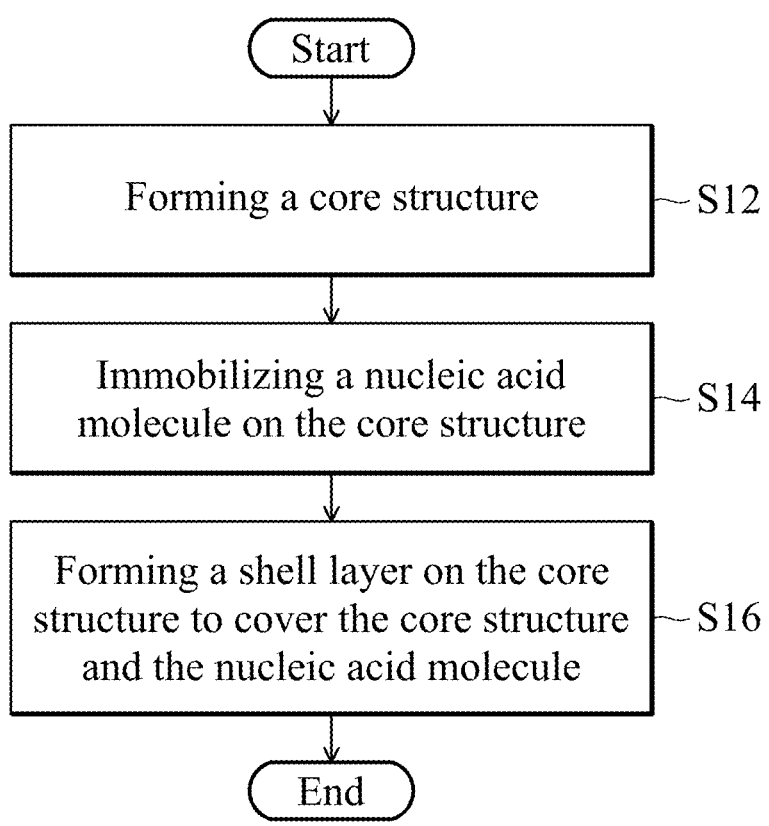
FIG. 3 is a flowchart of a method of manufacturing the tracer particle in accordance with some embodiments of the present disclosure.

Next, refer to FIG. 3, which is a flowchart of a method 10M of manufacturing the tracer particle in accordance with some embodiments of the present disclosure. It should be understood that, in some embodiments, additional operations may be provided before, during and/or after the method of manufacturing the tracer particle. In some embodiments, some of the operations described may be replaced or omitted as needed. In some embodiments, the order of operations/steps may be interchangeable. The description of the following manufacturing method can be understood by referring to the structure of the tracer particle 20 shown in FIG. 2.

As shown in FIG. 3, in some embodiments, the method 10M for manufacturing the tracer particles may include forming a core structure 102 (step S12), immobilizing a nucleic acid molecule 104 on the core structure 102 (step S14), and forming a shell layer 106 on the core structure 102 (step S16) to cover the core structure 102 and the nucleic acid molecule 104. Specifically, in some embodiments, the step of forming the core structure 102 may further include providing an oil phase solution, providing an aqueous phase solution, and adding the oil phase solution to the aqueous phase solution to form a mixed solution. The oil phase solution may include a precursor of silicon and a co-emulsifier. In some embodiments, the precursor of silicon may include tetraethoxysilane (TEOS). In some embodiments, the co-emulsifier may include a C2 to C10 short chain alcohol, a non-ionic surfactant, or a combination thereof. In some embodiments, the C2 to C10 short chain alcohol may include isopropanol. In some embodiments, the ratio (volume ratio) of the precursor of silicon to the co-emulsifier may be in a range from about 5:1 to about 1:10, or from about 1:1 to about 1:10, for example, about 1:1.

In some embodiments, the oil phase solution may further include a solvent. In some embodiments, the solvent may include a C6 to C18 medium chain alkane, a C6 to C18 medium chain ester, toluene, or a combination thereof. In some embodiments, the C6 to C18 medium chain alkane may include octane. In some embodiments, the ratio (volume ratio) of the precursor of silicon to the solvent in the oil phase solution may be in a range from about 1:1 to about 1:15, or from about 1:3 to about 1:10, for example, about 1:7.

In some embodiments, the ratio (volume ratio) of the precursor of silicon, the co-emulsifier and the solvent in the oil phase solution may be in a range from about 3:1:1 to about 15:1:1, or from about 5:1:1 to about 10:1:1, for example, about 7:1:1. It should be understood that the proportion of precursor of silicon, co-emulsifier and solvent should be controlled within a specific range, so that the tracer particle that is formed can have good homogeneity, i.e. have a uniform shape, size, or particle size.

Furthermore, the aqueous solution may include water and a surfactant. In some embodiments, the surfactant may include organic ammonium salts, alkyl sulfates, fatty acid salts, or a combination thereof. In some embodiments, the organic ammonium salt may include hexadecyl trimethyl ammonium bromide (CTAB). In some embodiments, the ratio of water to surfactant in the aqueous solution may be in a range from about 1:1 to about 10:1, or from about 10:1 to about 30:1.

In some embodiments, the aqueous solution may be first heated to a temperature of about 50° C. to about 80° C., or about 55° C. to about 70° C., e.g., about 60° C., so that the surfactant may be dissolved in water, and then the oil phase solution may be added to the water phase solution.

Furthermore, in some embodiments, the step of forming the core structure 102 may further include adding a catalyst to the mixed solution, and heating the mixed solution. In some embodiments, the catalyst may include a basic solution. In some embodiments, the pH value of the catalyst may be in a range from about 8 to about 14. In some embodiments, the catalyst may include ammonia, sodium hydroxide, calcium hydroxide, potassium hydroxide, an alkaline liquid, or a combination thereof.

In some embodiments, the temperature for heating the mixed solution may be in a range from about 50° C. to about 80° C., or from about 55° C. to about 70° C., for example, about 60° C. Moreover, in some embodiments, the time of heating may be in a range from about 2 hours to about 4 hours, for example, about 3 hours. In some embodiments, after the mixed solution is heated, the mixed solution may be left at room temperature overnight, and then the supernatant may be removed by centrifugation, and the ultrasonic vibration extraction may be performed using ethanol to obtain the core structure 102 (the porous carrier of the tracer particle).

In some embodiments, after the step of heating the mixed solution, the method may further include a step of adding a surface modifier to the mixed solution to improve the dispersing ability of the porous carrier. In some embodiments, the surface modifier may include a quaternary ammonium salt containing chlorine, e.g., may include N-methyl-3-aminopropyltrimethoxyalkane (trimethoxy[3-(methylamino)propyl]silane, TMAPS). Specifically, in some embodiments, the core structure 102 obtained in the foregoing step S12 may be dissolved in the co-emulsifier (e.g., isopropanol), and the surface modifier may be added thereto and the mixture may be centrifuged after shaking, and then the supernatant may be removed and the product may be dissolved in water to achieve dispersion.

Next, in some embodiments, the core structure 102 obtained in the foregoing steps may be mixed with the nucleic acid molecule 104 and centrifuged after shaking to immobilize the nucleic acid molecule 104 on the core structure 102 (step S14). As described above, the nucleic acid molecule 104 may include deoxyribonucleic acid (DNA), ribonucleic acid (RNA), peptide nucleic acid (PNA), or a combination thereof. In some embodiments, the length of the nucleic acid molecule 104 may be in a range from about 10 base pairs to about 2000 base pairs. In some embodiments, the nucleic acid molecule 104 may be a plasmid and the length may be in a range from about 1500 base pairs to about 10,000 base pairs.

In some embodiments where the length of the nucleic acid molecule 104 ranges from about 10 base pairs to about 2000 base pairs, the ratio (volume ratio) of the core structure 102 to the nucleic acid molecule 104 may be in a range from about 1:1 to about 10:1, or from about 2:1 and about 8:1. In some embodiments where the length of the nucleic acid molecule 104 ranges from about 1500 base pairs to about 10,000 base pairs, the ratio (volume ratio) of the core structure 102 to the nucleic acid molecule 104 may be in a range from about 1:10,000 to about 1:1000, or from about 1:100 and about 1:1000.

In some embodiments, the core structure 102 having the nucleic acid molecule 104 immobilized thereon may be added to a mixed alcohol solution to continue the step of forming the shell layer 106 afterwards. In some embodiments, the alcohol mixed solution may include glycerol, ethanol and water. In some embodiments, the ratio (volume ratio) of glycerol, ethanol and water may be in a range from about 100:100:1 to about 300:300:1, or from about 100:100:1 to about 200:200:1.

Next, the shell layer 106 may be formed on the core structure 102 having the nucleic acid molecule 104 immobilized thereon. In some embodiments, the step of forming the shell layer 106 on the core structure 102 (step S16) may include mixing and shaking the core structure 102 having the nucleic acid molecule 104 immobilized thereon with the precursor of silicon and the surface modifier. In some embodiments, the precursor of silicon and the surface modifier may be added in two portions and shaken twice.

In some embodiments, the precursor of silicon may include tetraethoxysilane (TEOS). In some embodiments, the surface modifier may include a quaternary ammonium salt containing chlorine, e.g., may include N-methyl-3-aminopropyltrimethoxyalkane (trimethoxy[3-(methylamino)propyl]silane, TMAPS).

In some embodiments, the ratio (volume ratio) of the core structure 102 having the nucleic acid molecule 104 immobilized thereon, the precursor of silicon, and the surface modifier may be in a range from 1:1:1 to 100:50:1, or from 10:1:1 to 50:5:1.

A detailed description is given in the following particular embodiments in order to provide a thorough understanding of the above and other objects, features and advantages of the present disclosure. However, the scope of the present disclosure is not intended to be limited to the particular embodiments.

Example 1: Design of Specific Nucleic Acid Molecules

Sequence Design of Hybrid DNA

A 50 bp fragment of 16 S rDNA from *Tepidimonas fonticaldi* (strain AT-A2) and a 50 bp fragment of 18 S rDNA from *Chlamydomonas reinhardtii* (strain CC-621) were selected. 25 bp (16 S rDNA)-25 bp (18 S rDNA)-25 bp (16 S rDNA)-25 bp (18 S rDNA) were concatenated to synthesize a 100 bp of hybrid DNA sequence (SEQ ID No. 1) that has better temperature resistance than general DNA sequences. The hybrid DNA sequence (SEQ ID No. 1) served as a specific nucleic acid molecule.

Confirmation of Uniqueness of Hybrid DNA Sequence

The BLAST (Basic Local Alignment Search Tool) system of National Center for Biotechnology (NCBI) of the United States was used to confirm the uniqueness of the synthesized hybrid DNA sequence. The alignment results showed zero correlation (no significant similarity), which means that no similar DNA sequence exists in the database and proves that the designed hybrid DNA sequence was unique.

Example 2: Preparation of Unique Nucleic Acid Molecules

Gene synthesis company Integrated DNA Technologies was entrusted to synthesize the DNA sequence of SEQ ID No. 1 (100 bp). Based on the sequence of SEQ ID No. 1, a set of primer pairs of SEQ ID No. 2 and SEQ ID No. 3 were designed. The DNA sequence of SEQ ID No. 1 was used as a template, and the DNA sequences of SEQ ID Nos. 2 and 3 were used as the primers at the 3-terminal and 5-terminal (melting temperature Tm was 59° C. and 63° C., respectively), and the PCR process was performed. The DNA fragment of SEQ ID No. 1 was amplified to generate sufficient specific nucleic acid molecules for the subsequent step of immobilizing the nucleic acid molecules.

The materials used for the PCR process were as follows: 10 ng (1 μl) of template, 2 μl of 3-terminal and 5-terminal primers (10 μM), 25 μl of 2× Taq Master Mitrix, and 20 μl of ddH$_2$O. The total reaction volume was 50 μl. The temperature conditions for the PCR amplification reaction were set as follows: 95° C. reaction for 1 minute→[95° C. reaction for 1 minute→55° C. reaction for 30 seconds→72° C. reaction for 9 seconds] repeated for 12 cycles→72° C. reaction for 1 minute→stayed at 12° C.

Figure 4:
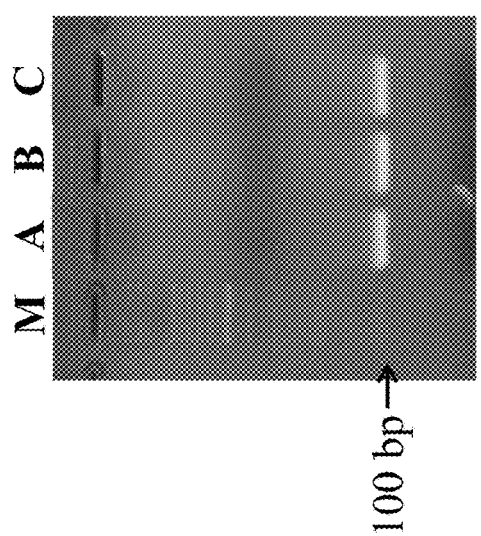
FIG. 4 shows the result of gel electrophoresis analysis of the target nucleic acid molecule tags in accordance with some embodiments of the present disclosure.

The gel electrophoresis analysis was used to confirm whether the obtained PCR product was the specific nucleic acid molecules as designed. The materials used in the gel electrophoresis process were as follows: 2.5% agarose, 10× TBE buffer (Tris-borate-EDTA). 1 kb DNA ladder (as marker, M) (CLUBIO) and 6× Loading dye (CLUBIO), and DNA electrophoresis system Mupid-2plus (Mupid) was used. The results of gel electrophoresis are shown in FIG. 4, and A to C in the figure were all PCR products, and M was 1 kb DNA ladder. As shown in FIG. 4, the length of the amplified PCR product was 100 bp, which was consistent with the DNA length of SEQ ID No. 1.

Next, Gel/PCR extraction Kit (Biomate) was used to purify the electrophoretic gel to remove dNTPs and primers that were not used in the PCR process to avoid affecting the subsequent DNA immobilization step. After the purification step, the DNA product of SEQ ID No. 1 was obtained.

Example 3: Preparation of Plasmids Including Unique Nucleic Acid Molecules

The target specific sequence (SEQ ID No. 1) was cloned using a T&A cloning vector (Yeastern biotech), and the recombinant plasmid (about 3 kb in length) was transferred to the host cell (*Escherichia coli*, DH5α). The host cells *E. coli* were then cultured in large quantities in the fermentation tank, and the bacterial cells were obtained by centrifugation, and then the plasmids including the desired target specific sequences were extracted from the bacterial cells using alkaline lysis.

Figure 5B:
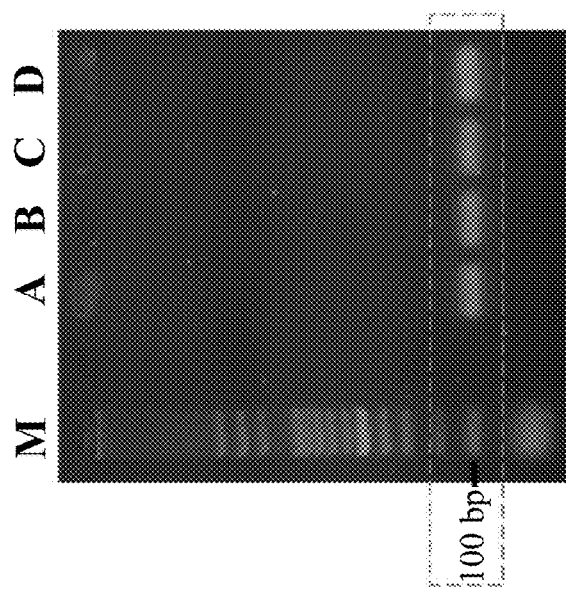
FIG. 5B shows the result of gel electrophoresis analysis of the target nucleic acid molecule tags in the plasmid products in accordance with some embodiments of the present disclosure.
Figure 5A:
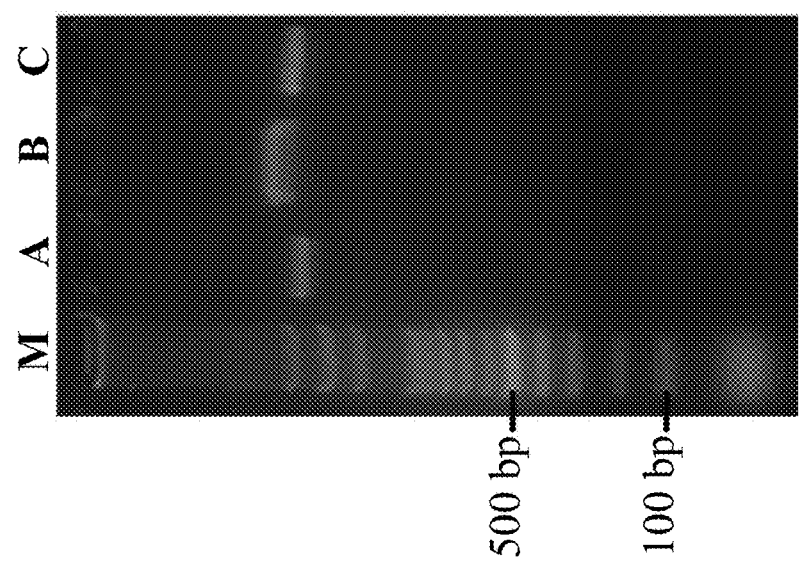
FIG. 5A shows the result of gel electrophoresis analysis of the plasmid products containing the target nucleic acid molecule tags in accordance with some embodiments of the present disclosure.

The restriction enzymes EcoRI and HindIII were used to cut the plasmids, and the length of the obtained plasmids was confirmed to be correct (approximately 3 kb) by gel electrophoresis analysis. The materials used in the gel electrophoresis process were as follows: 1.5% of agarose, 0.5× TAE buffer (Tris-Acetate-EDTA), 1 kb DNA ladder (as a marker, M) (CLUBIO), and 6× Loading dye (CLUBIO), and DNA electrophoresis system Mupid-2plus (Mupid) was used. The results of gel electrophoresis are shown in FIG. 5A, and A in the figure was the plasmid without cutting by restriction enzymes, B was the plasmid cut with EcoRI, C was the plasmid cut with HindIII, and M was a marker of 1 kb DNA ladder. As shown in FIG. 5A, the length of the plasmid obtained by culturing in *E. coli* was about 3 kb, which was consistent with the length of the original constructed plasmid.

Next, the obtained plasmid was used as a template, and the DNA sequences of SEQ ID Nos. 2 and 3 were used as 3-terminal and 5-terminal primers to perform the PCR process. The materials used in the PCR process were as follows: 10 ng (1 µl) of the template, 2 µl of 3-terminal and 5-terminal primers (10 µM), 25 µl of 2× Taq MasterMix, and 20 µl of ddH$_2$O. The total reaction volume was 50 µl. The temperature conditions for the PCR amplification reaction were set as follows: 95° C. reaction for 5 minutes→[95° C. reaction for 30 seconds→60.7° C. reaction for 30 seconds→72° C. reaction for 10 seconds] repeated for 29 cycles→72° C. reaction for 5 minutes→stayed at 4° C.

The gel electrophoresis analysis was used to confirm whether the PCR product obtained was the target specific sequence (SEQ ID No. 1). The materials used for the gel electrophoresis process were as follows: 2.5% agarose, 10× TBE buffer (Tris-borate-EDTA), 1 kb DNA ladder (as marker, M) (CLUBIO), and 6× Loading dye (CLUBIO), and DNA electrophoresis system Mupid-2plus (Mupid) was used. The results of gel electrophoresis are shown in FIG. 5B, and A to D in the figure were all PCR products, and M was 1 kb DNA ladder. As shown in FIG. 5B, the length of the PCR amplified product was about 100 bp, which was consistent with the DNA length of SEQ ID No. 1.

Figure 6D:
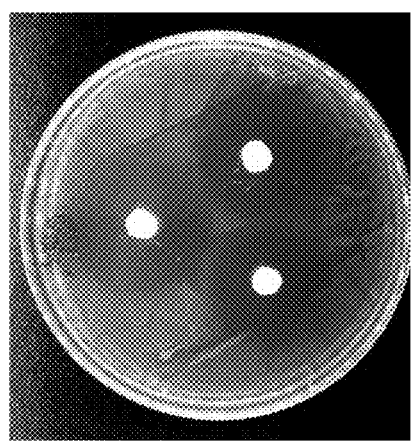
FIGS. 6A to 6D show the results of the toxicity test of DNA of SEQ ID NO. 1 on microorganisms in accordance with some embodiments of the present disclosure.
Figure 6C:
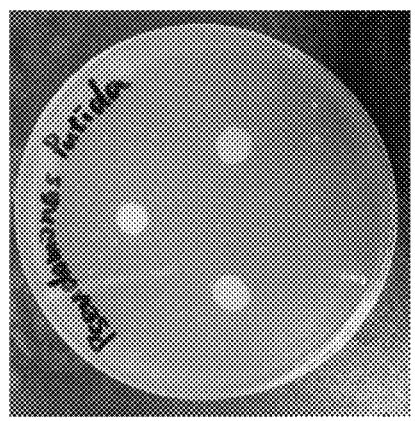
Figure 6B:
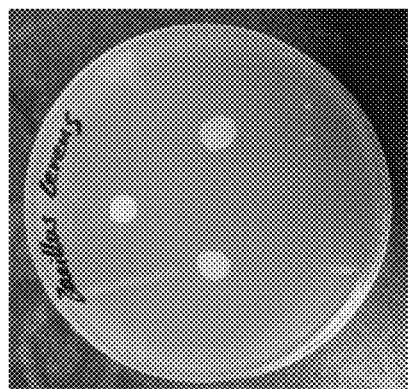
Figure 6A:
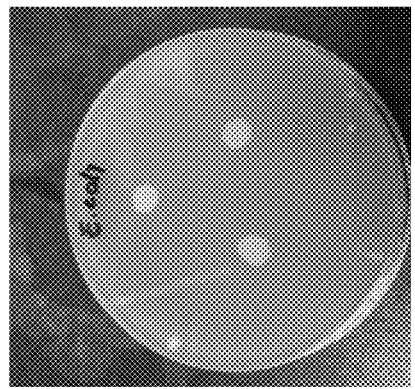

Test Example 1: Risk Assessment of Synthesized Specific Nucleic Acid Molecules on Environment and Human The synthesized DNA sequence of SEQ ID No. 1 was tested to determine whether it has an inhibitory effect on microorganisms in the environment by using the toxicity test of environmental strains. The results are shown in FIGS. 6A to 6D, and FIG. 6A, FIG. 6B and FIG. 6C respectively show the toxicity results of the synthesized DNA sequence on *E. coli*, *Bacillus cereus*, and *Pseudomonas putida*. FIG. 6D was a control group where *E. coli* was inhibited. According to the above results, it can be seen that the synthesized DNA sequence of SEQ ID No. 1 did not have an inhibitory effect on microorganisms commonly found in the environment.

Furthermore, the sequence of SEQ ID No. 1 was compared with the sequence of the human chromosome (Human G+T), and the comparison result showed that E-value>>1 (value), and the similarity was zero (if E-value<10$^{-5}$, it represents high homology). Therefore, the risk of the sequence of SEQ ID No. 1 replacing human genes was close to zero. In addition, the sequence of SEQ ID No. 1 was further divided into four 25 bp fragments for comparison. The comparison results showed that E-value>1, the similarity was extremely low, and the risk of replacing human genes was also close to zero.

Example 4: Preparation of Tracer Particle A

Preparation of Core Structure and Surface Modification

The corn starch and deionized water were used to prepare 35% starch suspension, and the mixture was stirred at 35° C. The pH value of the starch solution was adjusted to 9.5 using 0.5N NaOH. Next, 20 g of sodium hypochlorite was taken and slowly added to the starch solution (addition time was longer than 30 minutes), and 1N HCl was used to maintain the pH value of the starch solution at 9.5. After sodium hypochlorite was added, the starch solution was continued stirring for 50 minutes, and the pH value of the starch solution was maintained at 9.5 using 0.5N NaOH. After the reaction was completed, the pH value of the starch solution was adjusted to 7 with 1N HCl, and then washed with ddH$_2$O and alcohol, filtered with suction, and dried in an oven at 50° C. to obtain the modified starch.

22 mL of tetraethoxysilane (TEOS) was added to 36 mL of deionized water and 1 mL of 2% HCl, and was stirred until the mixture hydrolyzed and transparent. Next, after adding 3 g of the modified starch described above, 20 mL of 5% NH$_4$OH was slowly dropped into the mixture using the separatory funnel and then stirred for 40 minutes. The solid was filtered and dried in an oven at 50° C. for 24 hours. Thereafter, the solid was calcined at a high temperature of 550° C. and held at 550° C. for 3 hours. Here, a porous carrier (core structure) of the tracer particle was obtained.

2 g of the above porous carrier was added to 20 mL of isopropanol and uniformly dispersed, and then 0.889 mL of N-methyl-3-aminopropyltrimethoxyalkane (trimethoxy[3-(methylamino)propyl]silane, TMAPS) and 1 mL of deionized water were added, and stirred at 40° C. for 2 hours. Next, the mixture was centrifuged at 15275 RCF (relative centrifugal force) for 10 minutes, and the supernatant was removed. The remaining solid was dispersed in 40 mL of deionized water. Here, a surface-modified porous carrier was obtained.

Immobilization of Nucleic Acid Molecules

35 µL of the surface-modified porous carrier was taken and added to 10 µL of the DNA product (300 ppm) (or 1300 ppm) of SEQ ID No. 1. The mixture was shaken using a shaker, and then centrifuged at 18000 RCF for 10 minutes. Thereafter, the supernatant was taken out, washed several times with ddH$_2$O, and the solid was dispersed in 500 µL of ddH$_2$O.

Encapsulation of the Shell Layer

Next, 0.6 µL of N-methyl-3-aminopropyltrimethoxyalkane (trimethoxy[3-(methylamino)propyl]silane, TMAPS) and 0.6 µL of TEOS were added and shaken at 900 rpm for 4 hours. After that, 4 µL of TEOS was added and shaken at 900 rpm for 96 hours. Next, the mixture was centrifuged at 19375 RCF for 10 minutes, the supernatant was removed, and washed several times with ddH$_2$O. The solid was then dispersed in 45 µL of ddH$_2$O. Here, the preparation of tracer particle A was completed.

Figure 7A:
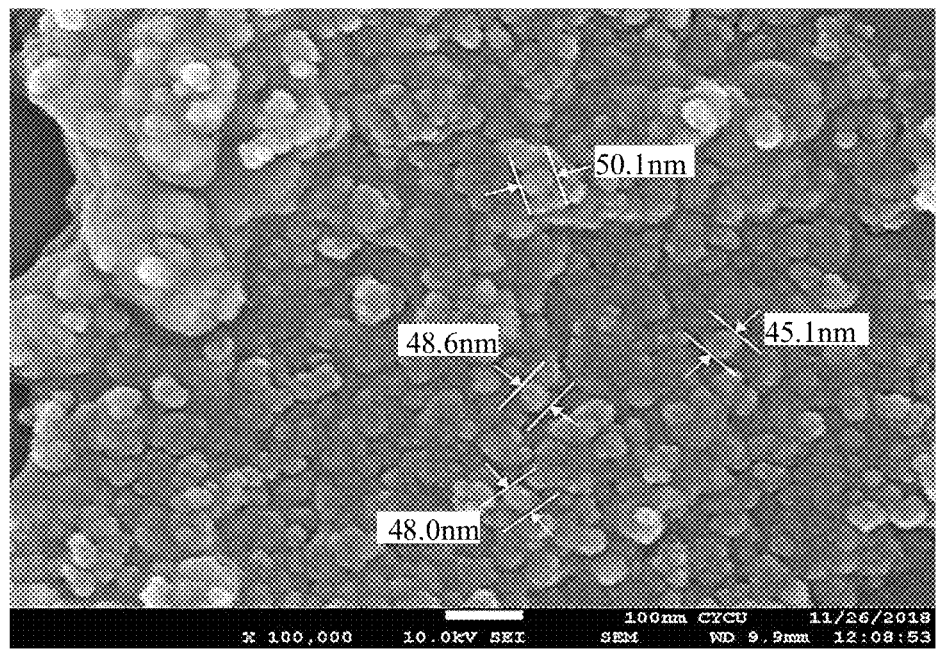
FIGS. 7A and 7B respectively are diagrams of the core structure before and after the encapsulation process of the shell layer observed using a scanning electron microscope (SEM) in accordance with some embodiments of the present disclosure.
Figure 7B:
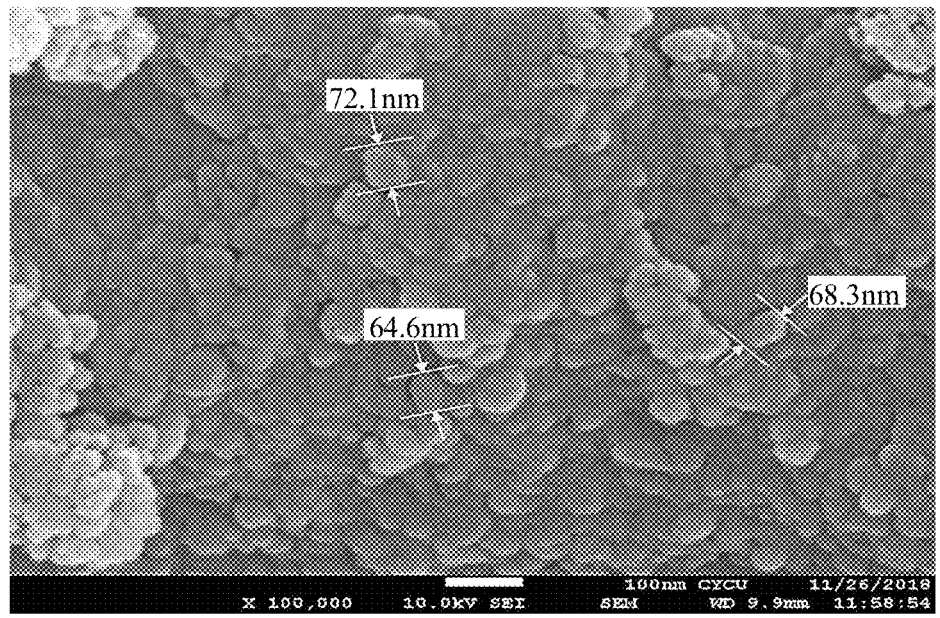

FIGS. 7A and 7B respectively are diagrams of the porous carrier before and after the encapsulation process of the shell layer observed using a scanning electron microscope (SEM). According to the results of SEM analysis, it was observed that the particle size of the tracer particles was about 40 nm to 50 nm before the encapsulation process (as shown in FIG. 7A), and increased to about 60 nm to 75 nm after the encapsulation process (as shown in FIG. 7B).

Example 5: Preparation of Tracer Particle B

Preparation of Core Structure and Surface Modification 2 g of hexadecyl trimethyl ammonium bromide (CTAB) and 30 ml of ddH$_2$O were used to prepare an aqueous solution in a serum bottle, and the aqueous solution was heated to 60° C. for dissolution. In addition, 7.2 ml of octane, 1 ml of tetraethoxysilane (TEOS), and 1 ml of isopropanol were used to prepare an oil phase solution, and the oil phase solution was added dropwise to the aqueous phase solution with a dropper. Next, 0.022 ml of 25% ammonia water was added and reacted at 60° C. for 3 hours. After the reaction was completed, the mixture was left at room temperature overnight. Thereafter, the mixture after reaction completed was centrifuged and the supernatant was removed, and the oil phase solution was replaced by ultrasonic vibration extraction with ethanol. Here, a porous carrier (core structure) of the tracer particle was obtained.

After centrifuging the above the porous carrier, it was added to 20 mL of isopropanol and uniformly dispersed.

Then, 0.222 mL of N-methyl-3-aminopropyltrimethoxyalkane (TMAPS) was added and shaken with a shaker four 18 hours. Thereafter, the mixture was centrifuged at 15275 RCF (relative centrifugal force) for 10 minutes, and the supernatant was removed. The solid was then dispersed in 20 mL of ddH$_2$O. Here, a surface-modified porous carrier was obtained.

Immobilization of Nucleic Acid Molecules

350 μL of the surface-modified porous carrier was added to the plasmid product including the sequence of SEQ ID No. 1 (100 μl) prepared in the above Example 3. After centrifuged at 15275 RCF for 10 minutes, the supernatant was removed, and the solid was dissolved in 5 ml of an alcohol mixed solution (glycerol:ethanol:water=150:150:1).

Encapsulation of the Shell Layer

Next, 6 μl of TMAPS and 6 μl of TEOS were added, and shaken with a shaker for 4 hours, and then 40 μl of TEOS was added and shaken with a shaker for 4 days. Thereafter, 24 μl of TMAPS was added and shaken with a shaker for 18 hours, and the solution was replaced with ddH$_2$O. Here, the preparation of tracer particle B was completed.

Figure 8A:
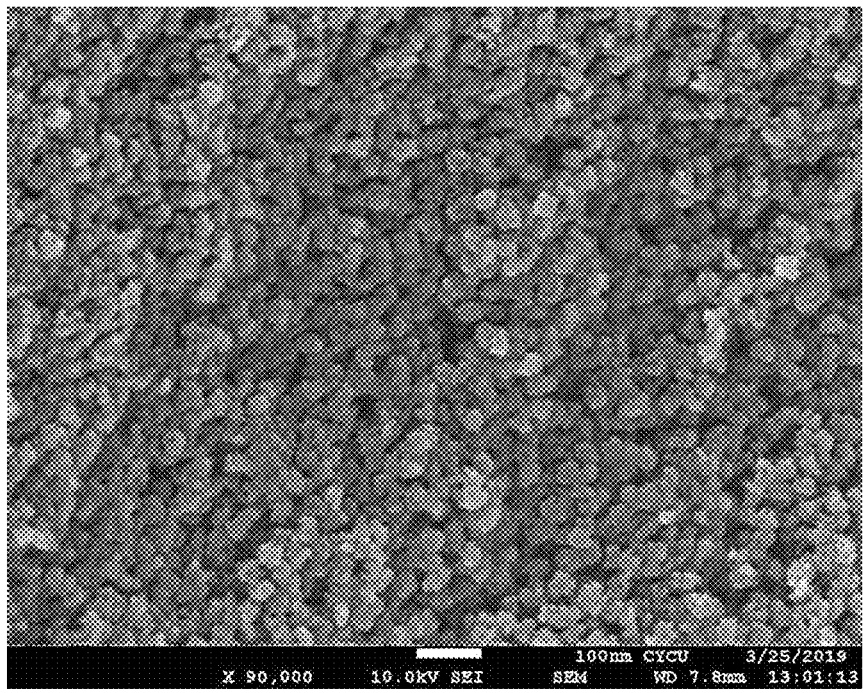
FIGS. 8A and 8B respectively are diagrams of the core structure before and after the encapsulation process of the shell layer observed using a scanning electron microscope (SEM) in accordance with some embodiments of the present disclosure.
Figure 8B:
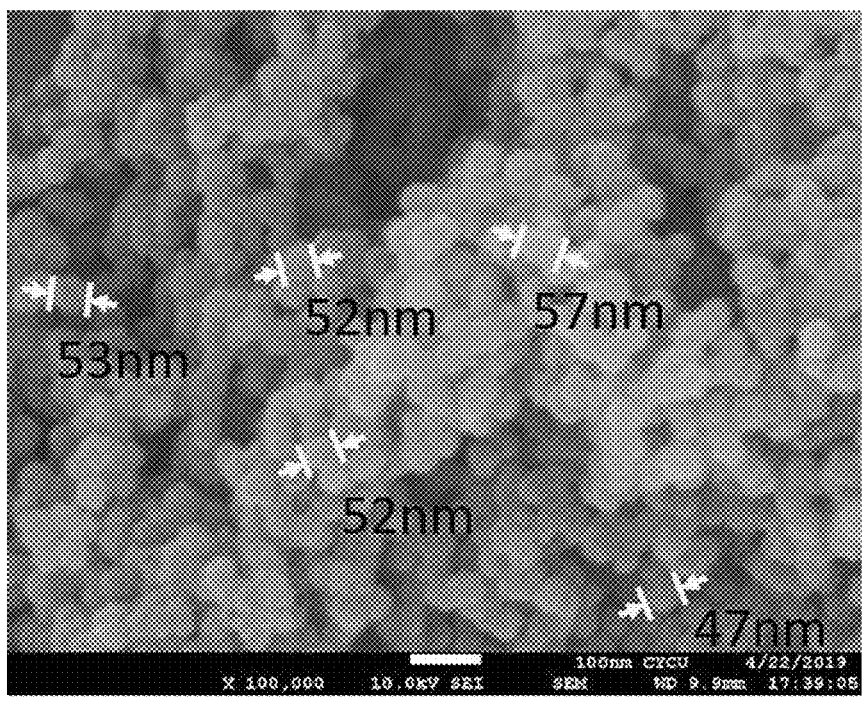

FIGS. 8A and 8B respectively are diagrams of the porous carrier before and after the encapsulation process of the shell layer observed using a scanning electron microscope (SEM). According to the results of SEM analysis, it was observed that the particle size of the tracer particles was about 30 nm to 40 nm before the encapsulation process (as shown in FIG. 8A), and increased to about 50 nm to 60 nm after the encapsulation process (as shown in FIG. 8B).

Comparative Example 1: Preparation of Tracer Particle C

The preparation method of the tracer particle C was substantially similar to that of the tracer particle A of Example 4. However, the tracer particle C was not encapsulated by the shell. That is, the DNA of the tracer particle C was exposed.

Comparative Example 2: Preparation of Tracer Particle D

The preparation method of the tracer particle D was generally referred to the Stöber Method (1968), and the results of the study by Kim et al. (T. G. Kim et al., 2017). First, 50 ml of 95% alcohol in addition to 60 ml of ddH$_2$O solution were prepared and stirred at a fixed speed of 450 rpm for 15 minute. 20 ml of TEOS was then added to mixture and hydrolyzed for 30 minutes, and finally 6 ml of 25% ammonia water was added and stirred for 2 hours for polymerization. After the reaction was completed, the liquid was centrifuged at 15275 RCF for 15 minutes, and the supernatant was removed. Then the solid was washed 3 times with 95% alcohol and placed in an oven at 50° C. to dry. Compared to the porous carrier of the tracer particle A, the carrier of the tracer particle D was a dense solid carrier with a porosity close to zero.

Example 6: Desorption Process of Nucleic Acid Molecules

The shell layer that protects the DNA was removed using hydrofluoric acid (HF), and the DNA was desorbed. 10 μL of the encapsulated tracer particles were then added to 40 μL of 1.5% HF/NH$_4$F aqueous solution, and the mixture was mixed for about 5 minutes. Thereafter, the desorbed DNA was recovered using a DNA purification kit (Bioman Scientific).

Example 7: Analysis of Recovered Nucleic Acid Molecules

The quantitative analysis of the recovered DNA was performed using a real-time polymerase chain reaction (q-PCR) analysis to confirm whether it contained the designed specific DNA sequence, and the concentration (mass) of the recovered DNA was measured simultaneously. The materials used for the q-PCR process were as follows: 1 μl of template (desorbed DNA after recovered), 0.75 μl of 3-terminal primer (10 μM) (SEQ ID No. 2), 0.75 μl of 5-terminal primer (10 μM) (SEQ ID No. 3), 12.5 μl of 2× SYBR Green Master Mix (Thermo Fisher Scientific) and 10 μl of ddH$_2$O. The total reaction volume was 25 μl. The temperature conditions for the q-PCR amplification reaction were set as follows: 95° C. reaction for 10 minutes→[95° C. reaction for 15 seconds→60° C. reaction for 9 seconds] repeated for 40 cycles→stayed at 12° C.

Test Example 2: Temperature Resistance Test of Tracer Particles

The tracer particles A prepared in the above Example 4 and the tracer particles C prepared in Comparative Example 1 were respectively placed in an oil bath at temperatures of 25° C., 100° C., 120° C., 140° C., 160° C., 180° C. and 200° C. for heating for 20 minutes. Next, the tracer particles were taken out, and the DNA remaining thereon was recovered and analyzed by gel electrophoresis.

Figure 9A:
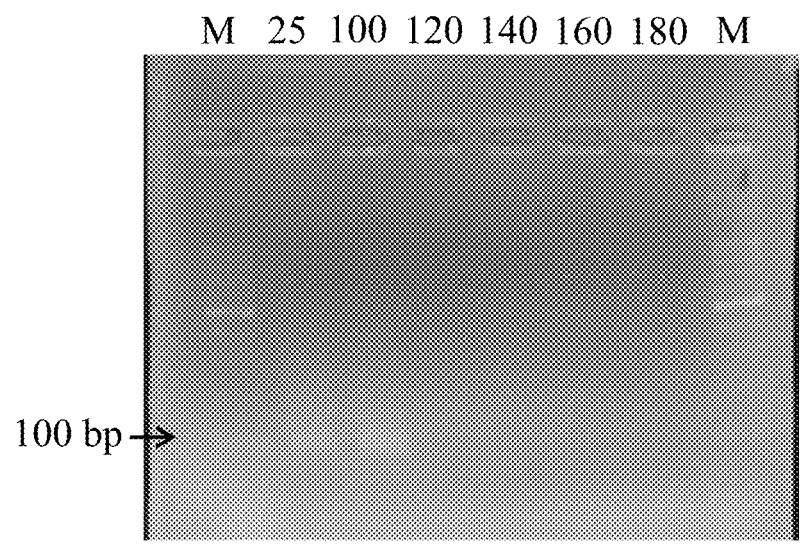
FIGS. 9A and 9B show the results of temperature resistance tests of the tracer particles in accordance with some embodiments of the present disclosure.
Figure 9B:
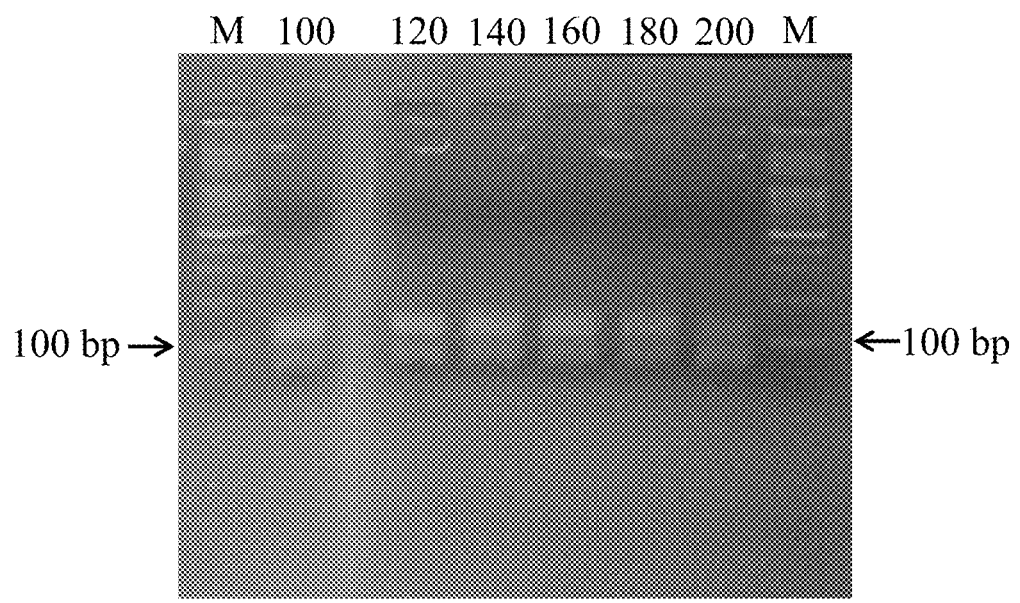

The results are shown in FIGS. 9A and 9B. FIGS. 9A and 9B show the results of temperature resistance tests of the tracer particles prepared in Comparative Example 1 and Example 4, respectively. The numbers 25, 100, 120, 140, 160, 180 and 200 denoted in the figures represented heating temperatures, and M was a marker (1 kb DNA ladder). From the results of FIGS. 9A and 9B, it can be seen that the high-temperature resistance of the tracer particle C (exposed DNA) of Comparative Example 1 reached about 100° C., and the high-temperature resistance of Example 4 (encapsulated DNA) reached about 200° C.

In addition, the temperature resistance of the tracer particles A of Example 4 at 120° C. was further tested. Specifically, the DNA recovery rate was measured at different time points, and the results are shown in Table 1 below.

TABLE 1

| Time (hours) | Recovery rate (%) |
|---|---|
| 0.0 | 100 |
| 0.1 | 100 |
| 0.5 | 100 |
| 1.0 | 96.5 |
| 1.5 | 97.2 |
| 2.0 | 90.9 |
| 2.5 | 79.4 |
| 5.0 | 76.5 |

According to the results shown in Table 1, it can be seen that the DNA recovery rate of the encapsulated tracer particles A could still be maintained at 76.5% after heating for 5 hours.

In addition, the temperature resistance of the tracer particles B of Example 5 at 120° C. was further tested. The DNA recovery was measured at different time points, and the results are shown in Table 2 below.

TABLE 2

| Time (hours) | Recovery rate (%) |
| --- | --- |
| 0.0 | 100 |
| 3 | 95.2 |
| 6.0 | 88.1 |
| 10.0 | 86.3 |
| 24.0 | 81.5 |

According to the results shown in Table 2, it can be seen that the DNA recovery rate of the encapsulated tracer particle B could still be maintained at 81.5% after heating for 24 hours.

Test Example 3: Comparison of the Temperature Resistance of Tracer Particles

The tracer particles A prepared in the above Example 4 and the tracer particles D prepared in the Comparative Example 2 were heated in an oil bath at 120° C. Next, after heating for 1, 2 and 2.5 hours, the tracer particles were taken out and the DNA remaining thereon was recovered. The remaining DNA content was measured and the remaining rate was calculated, and the results are shown in Table 3 below.

TABLE 3

| Time (hours) | Remaining rate of tracer particles A (%) | Remaining rate of tracer particles D (%) |
| --- | --- | --- |
| 0.0 | 100.0 | 100.0 |
| 1.0 | 96.5 | 74.1 |
| 2.0 | 90.9 | 54.1 |
| 2.5 | 79.4 | 52.4 |

According to the results shown in Table 3, it can be seen that after heating at 120° C. for 2.5 hours, the DNA remaining rate of the tracer particle A prepared in Example 4 was 79.4%, and the DNA remaining rate of the tracer particle D prepared in Comparative Example 2 was 52.4%. It can be seen that, compared with the tracer particle D having a solid carrier (without porosity), the tracer particle A having a porous carrier structure had improved resistance to high temperature.

Test Example 4: Acid and Alkali Resistance Tests of Tracer Particles

The tracer particles A prepared in the above Example 4 were placed in solutions having different pH values to test the resistance of the structure of the tracer particles A to acidic and alkaline environments. Sulfuric acid and alkaline solutions were used to prepare acidic and alkaline solvents, respectively. The tracer particles were placed in a solution of pH 1, pH 3, pH 5, pH 7, pH 9 and pH 13 for 60 minutes. Then, the tracer particles were taken out, and the DNA remaining thereon was recovered and analyzed by gel electrophoresis.

Figure 10:
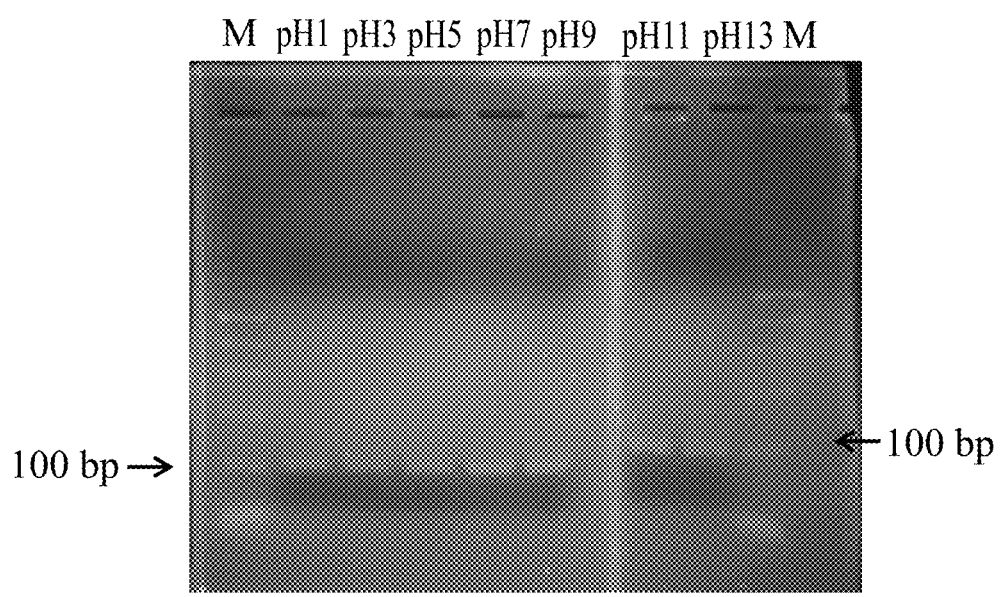
FIG. 10 shows the result of acid and alkali resistance test of the tracer particles in accordance with some embodiments of the present disclosure.

The results are shown in FIG. 10, and M in the figure was a marker (1 kb DNA ladder). According to the results shown in FIG. 10, it can be seen that the amount of DNA of the tracer particles A was barely reduced in the range of pH 9 or less. The amount of DNA of the tracer particles A was not affected by the change in pH and did not decrease significantly in the range above pH 9. From the above results, it can be seen that the tracer particles A of Example 4 had the ability to resist strong acids and strong alkalis.

Moreover, the tracer particles B of Example 5 were also tested for resistance to acid and alkali. The tracer particles B were placed in a solution having different pH values to test the resistance of the structure of the tracer particles B to acidic and alkaline environments. Sulfuric acid and alkaline solutions were used to prepare acidic and alkaline solvents, respectively. The tracer particles were placed in a solution of pH 1, pH 3, pH 5, pH 7, pH 9 and pH 13 for 24 hours. Then, the tracer particles were taken out, and the DNA remaining thereon was recovered. The remaining DNA content was measured and the remaining rate was calculated, and the results are shown in FIG. 11.

Figure 11:
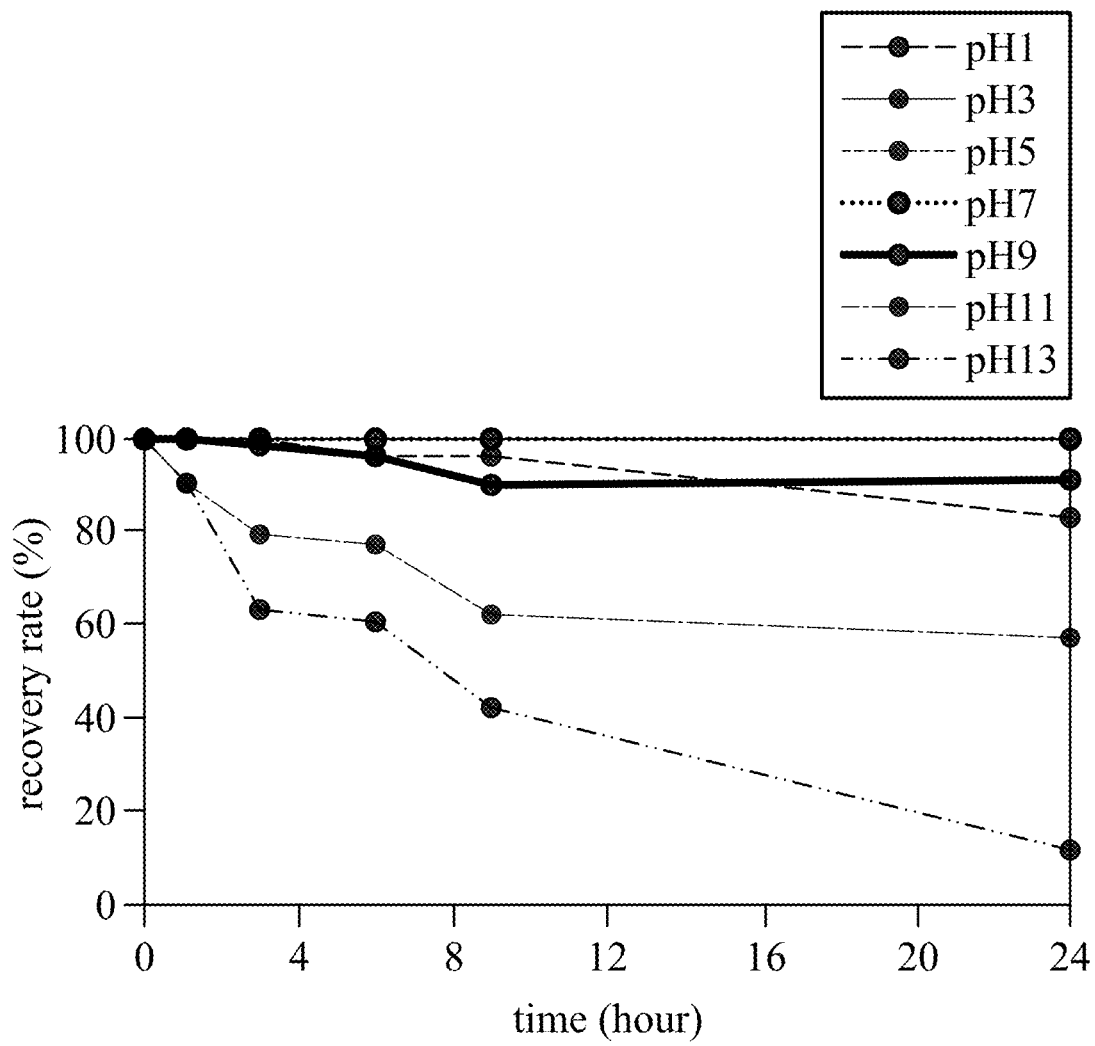
FIG. 11 shows the result of acid and alkali resistance test of the tracer particles in accordance with some embodiments of the present disclosure.

According to the results shown in FIG. 11, it can be seen that the amount of DNA of the tracer particles B was barely reduced in the range of pH 9 or less within 1 hour (the lines of pH 3, pH 5 and pH 7 in the figure overlapped). The amount of DNA of the tracer particles B was not affected by the change in pH and did not decrease significantly in the range above pH 9, which showed that the tracer particles B had the ability to resist strong acids and strong alkalis. It should be noted that after 24 hours of reaction, the amount of DNA of the tracer particles B also did not decrease significantly in the range below pH 9, indicating that the tracer particles B had the ability to resist strong acids for a long time.

Test Example 5: Temperature Resistance Test of Tracer Particles to Hot Water From Actual Fields The nanoporous carriers prepared in the above Example 5 were used to immobilize the plasmids that were constructed to include the target DNA tags, and the tracer particles B were produced after the encapsulation process. The tracer particles B were placed in a small reaction tank, and the hot water in the actual field was added inside. The hot water in the actual field was geothermal water from a volcanic geothermal area (Datun Mountain geothermal water, New Taipei City, pH 1.5, total dissolved solids in the water ~9200 ppm) and geothermal water from metamorphic rock geothermal area (Yilan Renze geothermal water, pH 8.8, and Yilan Renze geothermal water that was adjusted to pH 13 with ammonia water, total dissolved solids in water ~4000 ppm). They were individually placed in an oil bath at 120° C. and heated. Next, after heating for 480 and 720 hours, the tracer particles were taken out and the DNA remaining thereon was recovered. The remaining DNA content was measured and the remaining rate was calculated. The results are shown in Table 4 below.

TABLE 4

| Time (hours) | DNA remaining rate of tracer particles B in Datun Mountain geothermal water (%) | DNA remaining rate of tracer particles B in Renze geothermal water without pH adjustment (%) | DNA remaining rate of tracer particles B in Renze geothermal water with pH adjustment to 13 (%) |
| --- | --- | --- | --- |
| 0.0 | 100.0 | 100.0 | 100.0 |
| 480 | 11.3 | 8.7 | 5.3 |
| 720 | 10.7 | 7.5 | 3.8 |

According to the results shown in Table 4, after heating at 120° C. for 720 hours, the DNA remaining rate of the tracer particles B in the acidic environment was 10.7%, and the DNA remaining rate of the tracer particles B in the weak alkaline environment was 7.5%, and the DNA remaining rate of the tracer particles B in a strong alkaline environment was 3.8%. It can be seen that the tracer particles B were already feasible in preliminary geothermal field applications.

Test Example 6: Column Tracing Test of Tracer Particles

In order to simulate the application of tracer particles in an actual field (in soil or rock formations), quartz sands (0.84 mm) of No. 20 sieve were filled into a glass pipe column with the diameter of 0.8 cm and the length of 10.7 cm to prepare a quartz sand column. Generally speaking, the hydraulic conductivity of the geothermal fluid channel (fracture) is about $10^{-7}$ to $10^{-2}$ m/sec, and the hydraulic conductivity of the prepared quartz sand column was about $3.4*10^{-5}$ m/sec. Next, the tracer particles A prepared in the above Example 4 were placed in water, and passed into the quartz sand column at a flow rate of 0.1 ml/min, and a sample flowing out of the column was collected.

Figure 12:
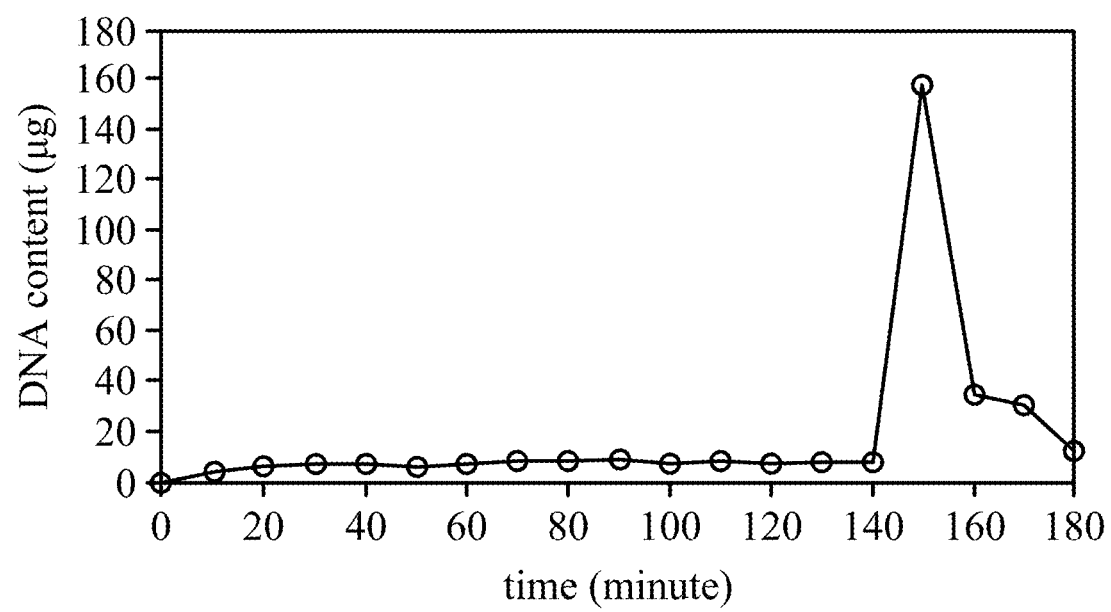
FIG. 12 shows the result of column tracing test of tracer particles in accordance with some embodiments of the present disclosure.

The purpose of the column tracing test was to investigate the effect of time on the recovery of tracer particles compared to the degree of diffusion. The results in FIG. 12 show the DNA content of the tracer particles A that were recovered over time. From the curve of the DNA content, it can be seen that after the tracer particles A were injected once, a small number of tracer particles A flowed out through the shortest channel due to advection, and most of the tracer particles A flowed out of the channel by spreading and diffusing due to the uneven distribution of the flow field (most of them flowed out at 140 minutes). The above transmission behavior was consistent with the results of common tracer tests. In addition, after measurement, the recovery rate of the tracer particles A could reach 97.5%, which indicated that the tracer particles in this embodiment would not be adsorbed by the quartz sand and could flow freely in the low-conductivity fluid channel.

To summarize the above, in accordance with some embodiments of the present disclosure, the tracer particles include specific nucleic acid molecules as indicators (tags, fingerprints), and the inorganic materials were used as the carrier and encapsulating materials. The core structure having a moderate porosity can increase the immobilized amount of nucleic acid molecules and reduce the thermal conductivity of the particles (reduces thermal resistance), thereby improving the temperature tolerance of the tracer particles. In addition, the tracer particles also have properties of resistance to acid and alkali, which can further improve the tolerance and recovery rate of the tracer particles in extreme environments.

Although some embodiments of the present disclosure and their advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps. In addition, each claim constitutes an individual embodiment, and the claimed scope of the present disclosure also includes the combinations of the claims and embodiments. The scope of protection of present disclosure is subject to the definition of the scope of the appended claims.

What is claimed is:

1. A tracer particle comprising:
   a core structure;
   a nucleic acid molecule immobilized on the core structure; and
   a shell layer covering the core structure and the nucleic acid molecule;
   wherein the core structure has a first porosity, the shell layer has a second porosity, and the first porosity is greater than the second porosity.

2. The tracer particle as claimed in claim 1, wherein the materials of the core structure and the shell layer comprise silicon dioxide, silicate, carbonate, nano-gold, metal oxide, polyethylene glycol polystyrene, polylactic acid, or a combination thereof.

3. The tracer particle as claimed in claim 1, wherein the first porosity is in a range from 2 nm to 100 nm.

4. The tracer particle as claimed in claim 1, wherein the second porosity is substantially zero.

5. The tracer particle as claimed in claim 1, wherein the second porosity is in a range from 0.5 nm to 10 nm.

6. The tracer particle as claimed in claim 1, wherein the shell layer is a single-layer structure or a multilayer structure.

7. The tracer particle as claimed in claim 6, wherein the multilayer structure comprises an outer shell layer and an inner shell layer, and the inner shell layer comprises a plurality of holes.

8. The tracer particle as claimed in claim 1, wherein the particle size of the tracer particle is in a range from 30 nm to 10000 nm.

9. The tracer particle as claimed in claim 1, wherein the particle size of the core structure is in a range from 20 nm to 9000 nm.

10. The tracer particle as claimed in claim 1, wherein the thickness of the shell layer is in a range from 10 nm to 5000 nm.

11. The tracer particle as claimed in claim 1, wherein the core structure comprises a plurality of holes, and the nucleic acid molecule is immobilized in the plurality of holes.

12. The tracer particle as claimed in claim 1, wherein the length of the nucleic acid molecule is in a range from 1500 base pairs (bp) to 10,000 base pairs.

13. The tracer particle as claimed in claim 1, wherein the nucleic acid molecule and the sequence as shown in SEQ ID No. 1 have a sequence similarity of at least 85%.

14. The tracer particle as claimed in claim 1, wherein the nucleic acid molecule comprises the sequence as shown in SEQ ID Nos. 2 and 3.

15. The tracer particle as claimed in claim 1, wherein the length of the nucleic acid molecule is in a range from 10 base pairs to 2000 base pairs.

16. A method for using a tracer particle, comprising:
    providing a tracer particle as claimed in claim 1;
    placing the tracer particle in a fluid to be observed;
    collecting a sample of the fluid, recovering the tracer particle from the sample, and releasing the nucleic acid molecule from the tracer particle; and
    analyzing the nucleic acid molecule that has been released.

17. The method for using a tracer particle as claimed in claim 16, wherein the method is used for fluid tracking in geothermal source or oil wells.

18. The method for using a tracer particle as claimed in claim 16, wherein the tracer particle can be operated in a fluid at 120° C. for at least 5 hours.

19. The method for using a tracer particle as claimed in claim 16, wherein the tracer particle can be operated in a fluid having a pH value of 1 to 13 for at least 60 minutes.

20. The method for using a tracer particle as claimed in claim 16, wherein the step of releasing the nucleic acid molecule from the tracer particle comprises using a hydrofluoric acid solution at a concentration of 0.5 (v/v) % to 3.0 (v/v) %.

21. The method for using a tracer particle as claimed in claim 16, wherein the step of analyzing the nucleic acid molecule that has been released comprises performing a real-time polymerase chain reaction (q-PCR).

* * * * *

SEQUENCE LISTING

```
<160> NUMBER OF SEQ ID NOS: 3

<210> SEQ ID NO 1
<211> LENGTH: 100
<212> TYPE: DNA
<213> ORGANISM: Artificial Sequence
<220> FEATURE:
<223> OTHER INFORMATION: Synthetic

<400> SEQUENCE: 1
taacgggtga cggaggatta gggttgctaa tacctggggc tgatgacggc gattccggag      60
agggagtaac ctgagagtac cgtaagaagc accggctaac                          100

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
taacgggtga cggaggatt                                                  19

<210> SEQ ID NO 3
<211> LENGTH: 22
```

```
<212> TYPE: DNA
<213> ORGANISM: Artificial Sequence
<220> FEATURE:
<223> OTHER INFORMATION: Synthetic

<400> SEQUENCE: 3
accgtaagaa gcaccggcta ac                                              22
```